(12) United States Patent
    Ditsios

(10) Patent No.: US 12,611,218 B2
(45) Date of Patent: Apr. 28, 2026

(54) DEVICE FOR TENSION BAND WIRING FIXATION OF FRACTURES, PARTICULARLY OF OLECRANON, AND OLECRANON OSTEOTOMY AND METHOD THEREFOR

(71) Applicant: ARISTOTLE UNIVERSITY OF THESSALONIKI-E.L.K.E. (Eidikos Logariasmos Kondilion Erevnas), Salonika (GR)

(72) Inventor: Konstantinos Ditsios, Plagiari Thermis (GR)

(73) Assignee: Aristotle University of Thessaloniki—E.L.K.E. (Eidikos Logariasmos Kondilion Erevnas), Salonika (GR)

( * ) Notice: Subject to any disclaimer, the term of this patent is extended or adjusted under 35 U.S.C. 154(b) by 0 days.

(21) Appl. No.: 18/575,721

(22) PCT Filed: Jun. 30, 2022

(86) PCT No.: PCT/GR2022/000034
    § 371 (c)(1),
    (2) Date: Dec. 29, 2023

(87) PCT Pub. No.: WO2023/275575
    PCT Pub. Date: Jan. 5, 2023

(65) Prior Publication Data
    US 2024/0315709 A1      Sep. 26, 2024

(30) Foreign Application Priority Data
    Jun. 30, 2021    (GR) .............................. 20210100445

(51) Int. Cl.
    A61B 17/17      (2006.01)
    A61B 17/15      (2006.01)
    A61B 17/88      (2006.01)
(52) U.S. Cl.
    CPC ........ *A61B 17/1739* (2013.01); *A61B 17/151* (2013.01); *A61B 17/1796* (2013.01); *A61B 17/8861* (2013.01)
(58) Field of Classification Search
    CPC .............. A61B 17/1739; A61B 17/151; A61B 17/1796
    See application file for complete search history.

(56) References Cited

U.S. PATENT DOCUMENTS 7,507,242 B2 *   3/2009   Triplett .................. A61B 90/94
                                                             606/87
2003/0187451 A1 *  10/2003  Ball .................... A61B 17/1739
                                                             606/87

(Continued)

FOREIGN PATENT DOCUMENTS

EP         1354562 A1    10/2003

OTHER PUBLICATIONS

International Search Report and Written Opinion for PCT Patent App. No. PCT/GR2022/000034 (Oct. 26, 2022).

*Primary Examiner* — Christian A Sevilla
(74) *Attorney, Agent, or Firm* — Cermak & McGowan LLP; Malcolm K. McGowan

(57)                ABSTRACT

The invention relates to the application of the tension-band-aiming device for olecranon fracture osteosynthesis. The device may also be used in cases where osteotomy of the olecranon is needed. It comprises a main part and five other adjuvant elements one of which assists for the osteotomy. The device offers precision for optimal results and is easy to use. The invention also relates to a method for the applica- (Continued)

tion of the tension-band-aiming device for olecranon fracture osteosynthesis and to its use.

19 Claims, 5 Drawing Sheets

(56) References Cited

U.S. PATENT DOCUMENTS

| | | | |
|---|---|---|---|
| 2010/0198228 A1* | 8/2010 | Thornes ............. | A61B 17/1796 |
| | | | 606/103 |
| 2011/0166574 A1* | 7/2011 | Hsu .................... | A61B 17/8861 |
| | | | 606/74 |
| 2020/0060690 A1* | 2/2020 | Woodard ............. | A61B 17/157 |

* cited by examiner (4a)

(4b)                              (4c)

(5a)

(5b)          (5c)

19

(6a)

(6b)

19

14

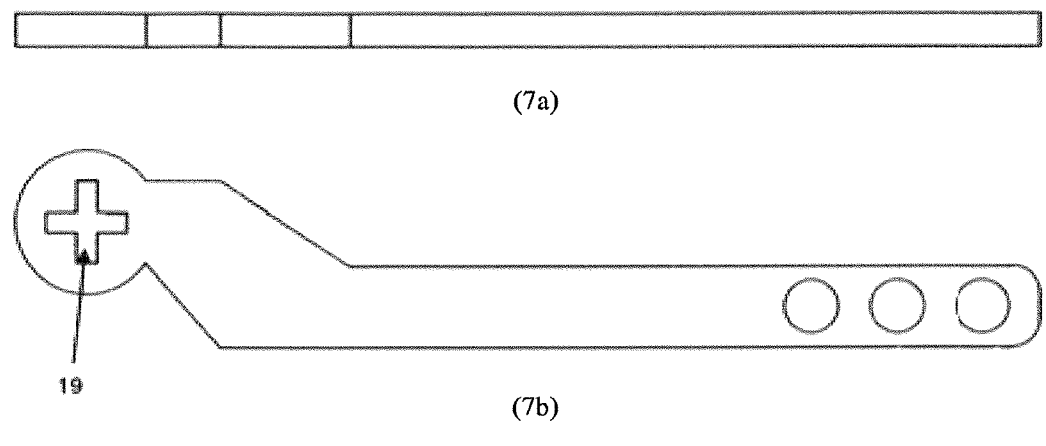
(7a)
19
(7b)
FIG. 7
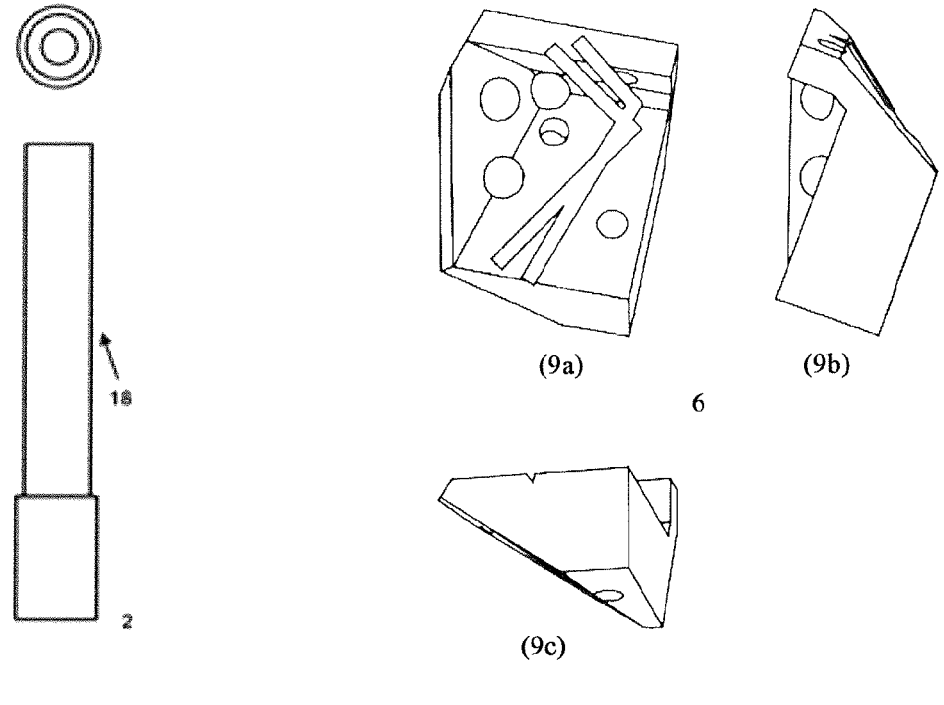
18
2
FIG. 8
(9a)          (9b)
6
(9c)
FIG. 9

DEVICE FOR TENSION BAND WIRING FIXATION OF FRACTURES, PARTICULARLY OF OLECRANON, AND OLECRANON OSTEOTOMY AND METHOD THEREFOR

CROSS-REFERENCE TO RELATED APPLICATIONS

This application claims priority from PCT/GR2022/000034, filed 30 Jun. 2022, which claims priority from Greek application No. 20210100445, filed 30 Jun. 2021. The contents of these priority applications are incorporated herein by reference in their entirety.

FIELD OF THE INVENTION

The invention relates to a device for the fixation of fractures, especially olecranon fractures, with a tension band wiring fixation.

BACKGROUND OF THE INVENTION

Olecranon fractures represent a relatively common injury in adults, of all ages with an estimated annual incidence of approximately 12 per 100.000 population or 40% of all fractures around the elbow joint.[1] Its subcutaneous location leaves it vulnerable to injury from a direct blow. Olecranon fractures account for approximately 10% of upper extremity fractures. Most of them occur in individuals after a fall from standing height. Younger patients are likely to have injuries related to a higher energy injury. Olecranon fractures frequently require surgical management.

Tension band wiring fixation is usually used in orthopedic trauma surgeries, such as for olecranon or patella fractures. This technique is also used to fix the iatrogenic olecranon osteotomy-fracture which is necessary when treating distal humerus fractures, with an annual incidence of approximately 5.7 per 100.000 population.[2]

The tension band technique has been used for many years in fractures. The indication is eccentrically loaded articular fractures.[3] Tension band wiring is a fixation technique which offers absolute stability. This technique provides both inter-fragmentary compression and direct bone healing. The principle makes use of the functional movement of the limb. Tension forces are converted into compression forces, provided the compression cortex is not deficient.[3] This technique is used most commonly in patella and olecranon fractures. Other indications are tuberosity of the humerus, the lateral and medial malleoli, and the trochanter of the femur.[3]

A simple transverse fracture can be fixed by placing a so-called K-wire through the fracture line[3], inserting a second K-wire parallel to the first one[3] with 1 cm between them; wherein the tension band is provided by a figure-of-eight looped wire over the tension surface, anchored around the K-wire ends proximally, and a transverse hole through the ulna distally. The wire is tightened simultaneously on both sides by twisting and turning to apply compression.[3]

This technique seems uncomplicated. It is readily available at a low cost and therefore presents a convenient operation technique that achieves excellent results. According to the international literature however, several publications support the notion that the tension band wiring technique is not as easy as the orthopaedic community suggests. Schneider et al.[1] described ten possible operative imperfections, thereby including non-parallel K-wires, long K-wires, K-wires extending radially outwards, insufficient fixation of the proximal ends of the K-wires, intramedullary K-wires, perforation of the joint surface, single wire knot, jutting wire knot(s), loose figure-of-eight configuration and incorrect repositioning.

PRIOR ART

Document WO2007/13361 of SYNTHES of Sep. 5, 2007 discloses a nail system for fixation of an olecranon osteotomy or fracture, which is placed in the intramedullary canal. Screws are applied proximally and distally through the nail and into the bone. In the present development, it is established not to use this type of osteosynthesis with intramedullary nail.

Initially, the simplest method that uses specific partial threaded screws, was described in 2017 by P. Le Guilloux, G. Larche and J-P. Podgorski in document EP 3320871 of Newclip Int. showing an equipment for treating the patella and olecranon fractures. The partial threaded screws are used to compress and stabilize the fracture line. However, it is chosen to use only Kirschner wires represented as K-wires and simple wires instead in the subject device.

Modifications to the classical method have been described, most notably by Huebner et al. to 1996 that use specialized bone pins for the easy passage of the wire during the application of the tension band technique. In particular, document U.S. Pat. No. 5,697,934 of Randall Huebner discloses a tension band wiring pin to repair the bone fracture which includes an elongated shaft with a leading end and a trailing end including a retaining band which comprises a middle region being configured in a specific manner. Again, it is chosen to use the classic Kirschner wires instead, in said development hereafter.

Document US2006/0200127 of Wardak Mohd of Jul. 9, 2006 discloses a method and an apparatus for the external fixation of bone fractures, especially fractures of the patella and the olecranon using a support member and a pair of tensioning assemblies and filaments. This is different however from applying internal osteosynthesis for olecranon fractures as intended in the development below.

Document US2009/0118770 of Robert Sixto of Jul. 5, 2009 discloses the application of an anatomical plate and locking or non-locking screws showing a system for the internal fixation of the olecranon fractures. This bone plate with holes is generally configurated to fit an anatomical surface of the bone region, and it is adapted to be customized to the shape of the bone. This kind of fracture fixation is different however from the intended technique wherein no plates or screws are applied.

At last, document US2009/0228009 of Scott Duncan of Oct. 9, 2009 discloses the use of a hybrid system of intramedullary nail and wire showing an olecranon fracture fixation system including an intramedullary core that is dimensioned for insertion in an intramedullary canal of the bone. A wire is applied proximally to the fracture through the nail and the bone, while only screws are applied distally. This kind of osteosynthesis with intramedullary nail is not used in the system presented hereafter.

CN209499881 U of 2019 10 18 discloses an orthopaedic Kirschner wire guiding device, especially for the orthopedics department. The device comprises a supporting rod, a sliding rod and a plurality of positioning sleeves, wherein one end of the sliding rod is connected with the supporting rod in a sliding mode, and the other end of the sliding rod is provided with a plurality of aiming holes next to one another, and wherein any one of the positioning sleeves can be inserted into any one of the aiming holes. A folding rod is arranged at the lower end of the supporting rod, the folding rod is parallel to the sliding rod, a plurality of positioning holes are formed in the folding rod, and the positioning holes are right opposite to the aiming holes.

Existing techniques for olecranon fracture osteosynthesis are accompanied by an abundance of complications. These problems can be solved with the application of the tension-band-aiming device for olecranon fracture osteosynthesis.

Aim of the Invention

The aim of the invention is to remedy these failures of the classical technique. In this respect, the main purpose of the invention is to facilitate the operation of orthopedic surgeons in applying the tension band wiring with greater accuracy and more reliable results.

SUMMARY OF THE INVENTION

According to the present invention, it is thus proposed to provide with the application of the tension-band-aiming device for olecranon fracture osteosynthesis as defined in claim 1. Accordingly, there is proposed a device for the fixation of fractures, especially olecranon fractures, with a tension band wiring fixation, which is remarkable in that it comprises a main member and a plurality of adjuvant elements, in particular five, one of which consists of an auxiliary means assisting for the osteotomy, wherein the main member is configured with a first part for handling the device and for connecting the 'vertical axis' element, an intermediary part which is formed with a set of different pairs of holes, particularly three, arranged mutually in line at the same distance of each other at the free end thereof for the external guides-sleeves to place K-Wires at a suitable angle depending on the morphology of the fracture, wherein the surgeon has the opportunity to stabilize with K-Wires even the most complex olecranon fractures with this plurality of pairs of holes, and a last part that is elongated and contains a plurality of apertures arranged in line for stabilizing said main part of the device and the cutting guide. The specific number of apertures is particularly greater than the number of said holes, more particularly not less than 10, yet more particularly 11. The number of holes is thus proposed only for an efficient stabilization of the device.

It further comprises a wire placing device that is composed of at least three arms respectively consisting of a first external arm which is fixed to said vertical axis and has said holes for a selective optional use, through which one sleeve is placed for drilling an ulnar shaft and for inserting a wire;

a second intermediary internal arm which has an elongated aperture, particularly oval like, and it is fixed to the vertical axis element with the elongated aperture for drawing the wire distally under the skin of the patient to be treated;

a third arm, particularly similar to the second, which is fixed likewise to the vertical axis element with the same function, wherein said three arms are in a mutually cooperating arrangement for the olecranon fractures osteosynthesis.

The device is also proposed for being used in cases where osteotomy of the olecranon is needed. It comprises a main part and five other adjuvant elements, one of which assists for the osteotomy. The device offers precision for optimal results and is easy to use.

Said document CN209499881 U discloses a device for fracture osteosynthesis which includes only some elements of the device according to the invention, such as merely the two arms, the sleeve guide for fitting K-Wires and the holes. However, this document does not disclose the entire device for fracture osteosynthesis, as defined above.

According to a particular embodiment of the device of the invention, all parts of the device are manufactured by being adapted to the device itself and to the requirements of the surgical technique.

It is chosen to use only Kirschner wires represented as K-wires and simple wires instead in the subject device.

According to a more particular embodiment of the device of the invention, said main part of the device is provided with a fastening element shaped as a cross connection referred to as said vertical axis element.

According to a yet more particular embodiment of the device of the invention, said part is connected to the central part of the device, by means of the cross shape of its center, wherein on either side thereof extensions are provided for connecting said internal and external arms.

According to a further particular embodiment of the device of the invention, it further comprises at least said wire placing device having its three arms respectively, wherein said first external arm has three holes for the selective use, through which said sleeve is placed allowing the insert of a wire, wherein said second intermediary internal arm has an elongated oval like hole and wherein said third arm is similar to the second which is fixed likewise to the vertical axis element with the same function for the olecranon fractures osteosynthesis.

According to a still more particular embodiment of the device of the invention, it further comprises sleeves-external guides for K-Wires that are cannulated and threaded, and that are fixed to said last part of said main member of the device, having a plurality of selectable positions with said apertures thereof, wherein these are placed parallel to each other and perpendicular to said ulnar bone.

According to an even more particular embodiment of the device of the invention, the latter member is associated with a sleeve as a cutting guide, wherein this element has three holes, one for sleeve position and two K-Wires sockets, for its stabilization and two guides for carrying out a V-shaped olecranon osteotomy for a correct olecranon osteotomy.

According to a twin embodiment of the device of the invention, two anatomical tension band aiming devices are provided, depending on whether it is intended for the right or left upper extremity.

Further particular embodiments of the device according to the invention are defined in the corresponding sub-claims depending thereon.

The failures of the classical technique of the known prior art above are thus deemed to be overcome thanks to the device of the invention.

The invention also relates to a method for the application of the tension-band-aiming device for olecranon fracture osteosynthesis and to its use, notably as defined in the corresponding method claims appended hereto.

Tension band wiring technique with a new aiming device has many advantages. First of all, it is a minimal invasive technique with high accuracy in fixation and reproducibility of the final result. This new device offers the opportunity for excellent results independently from the surgeon's experience. Moreover, the operating time is minimized and the necessity for a C-arm is diminished due to the device accuracy. The destructive complications from using the existing free hand technique are decreased, such as the cartilage damage during olecranon osteotomy.

To summarize, thanks to the invention, the operation of orthopedic surgeons in applying the tension band wiring is thus facilitated with greater accuracy and more reliable results.

The several advantages of the proposed device of this invention are recapitulated hereafter as consisting of involving a minimal invasive technique and it provides accuracy in fixation. It allows passing the wire subcutaneously and a reproducibility of the final result.

It further minimizes the necessity for a C-arm and it minimizes operating time. It involves less complication and it reduces the complications of free hand technique.

Finally, it provides accuracy in olecranon osteotomy, thereby avoiding any cartilage damage in olecranon Osteotomy taken place in non-cartilage area.

BRIEF DESCRIPTION OF THE DRAWINGS

FIG. 7 represents a top view and a side view of an external arm of the said wire placing device 5 with a series of longitudinally arranged holes in detail of the device according to the invention.

FIG. 8 shows the cannulated and threaded sleeve-external guide of the device for the K-wires.

FIG. 9 shows in three different detailed views 9*a*, 9*b* and 9*c* the cutting guide of the device used for olecranon osteotomy.

DETAILED DESCRIPTION OF THE INVENTION

Figure 1:
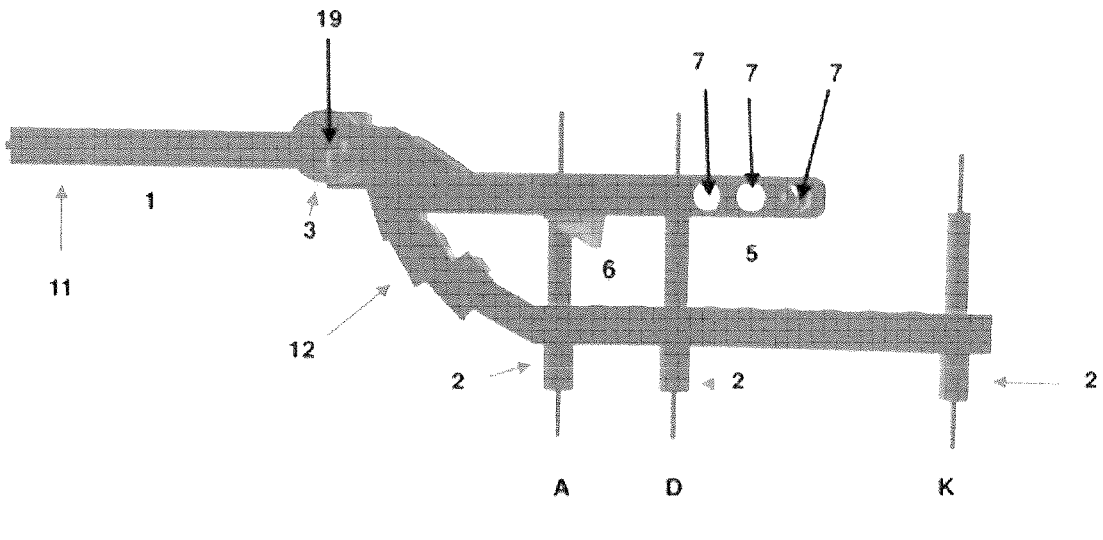
FIG. 1 is a side view showing the parts of the device according to the invention used for tension band wiring fixation for treating olecranon fractures.
Figure 2:
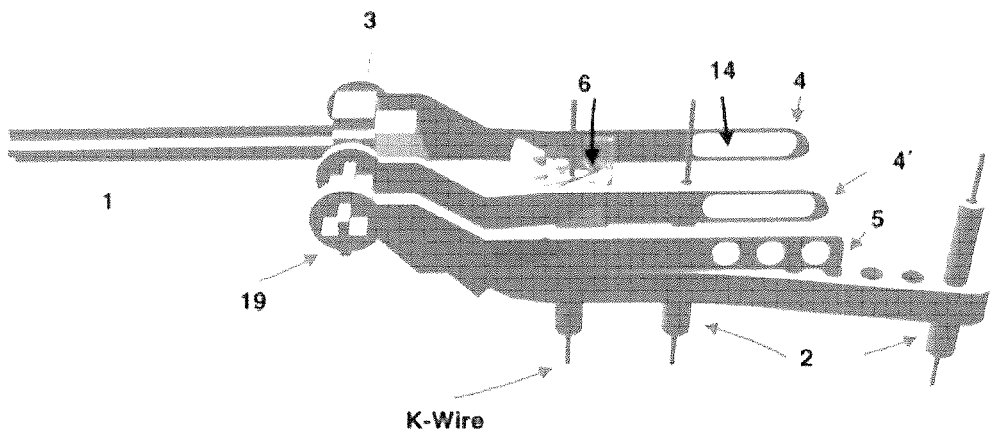
FIG. 2 is a 3D image with a top view of the device as described in FIG. 1 showing the parts of the device according to the invention.
Figure 3:
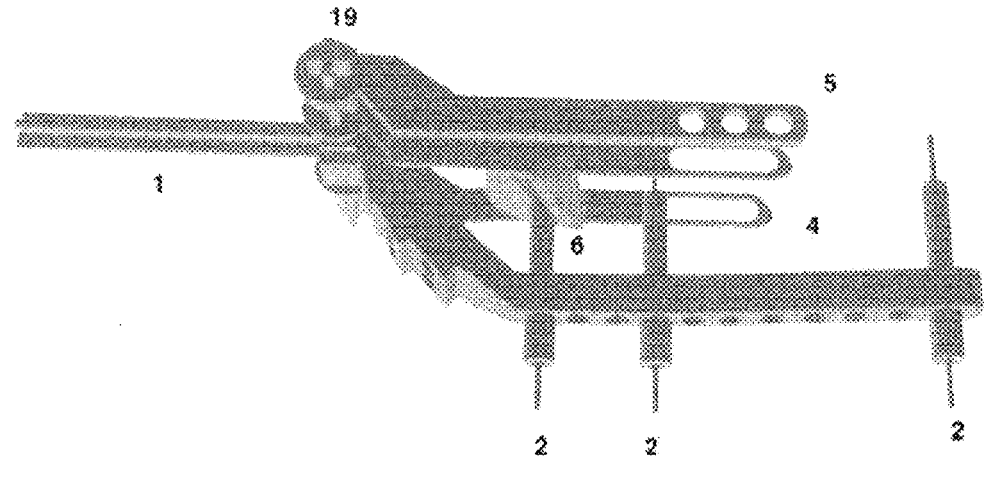
FIG. 3 is a perspective view of the device of the FIG. 2 showing the parts of the device according to the invention.

This invention relates to a device for fixation of fractures, especially of the olecranon fractures as shown in FIG. 1 representing the parts of the device used for tension band wiring fixation for treating olecranon fractures, as well as FIG. 2 and FIG. 3 each showing the parts of the device. There are two anatomical tension band aiming devices depending on whether it is the right or left upper extremity.

Figure 4:
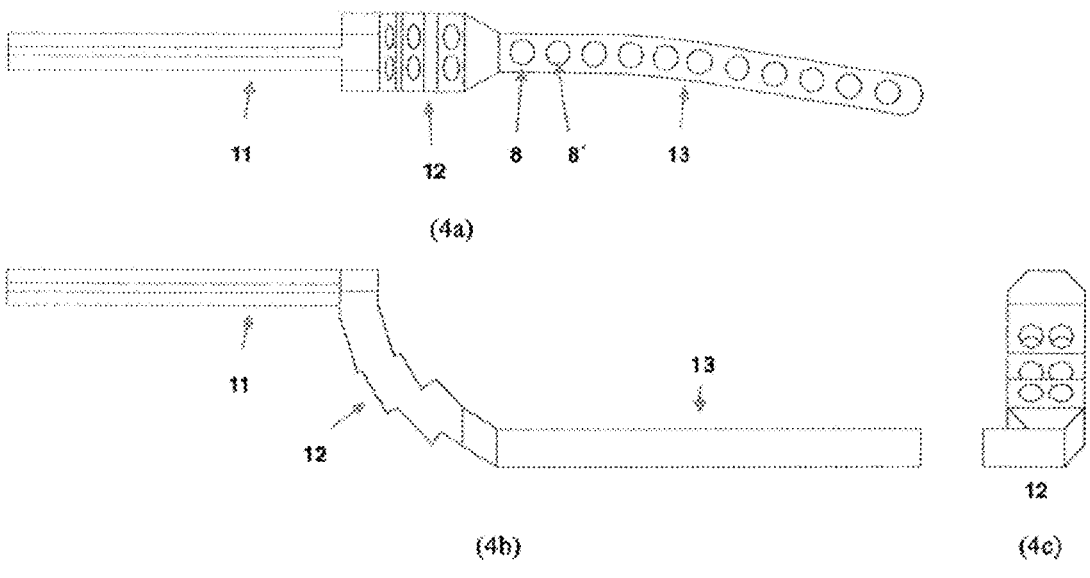
FIG. 4*a* represents a top view of the main member of the device used for tension band wiring fixation olecranon fracture cooperating with the element of the device according to the invention.
FIG. 4*b* is a side view of said main member of the device shown in FIG. 4*a* and FIG. 4*c* is a view in detail of the main member of the device shown in FIGS. 4*a* & 4*b*.

This device comprises a main member 1 which is configured as shown in FIG. 4 with a first part which is used for handling the device and for the connection of the vertical axis element 3, further with an intermediary part 5 wherein a plurality of holes is formed, in particular three different holes 7, 7', 7" arranged axially at the free end thereof at mutually same distance for the external guides-sleeves 18 to place K-wires 2 at a suitable angle depending on the morphology of the fracture. It further comprises an elongated part also containing a series of equidistant apertures, in particular eleven 8, . . . , 8ˣ, arranged axially at the free end thereof at mutually same distance, which is used to stabilize said main member of the device 1 and the cutting guide 6.

Figure 5:
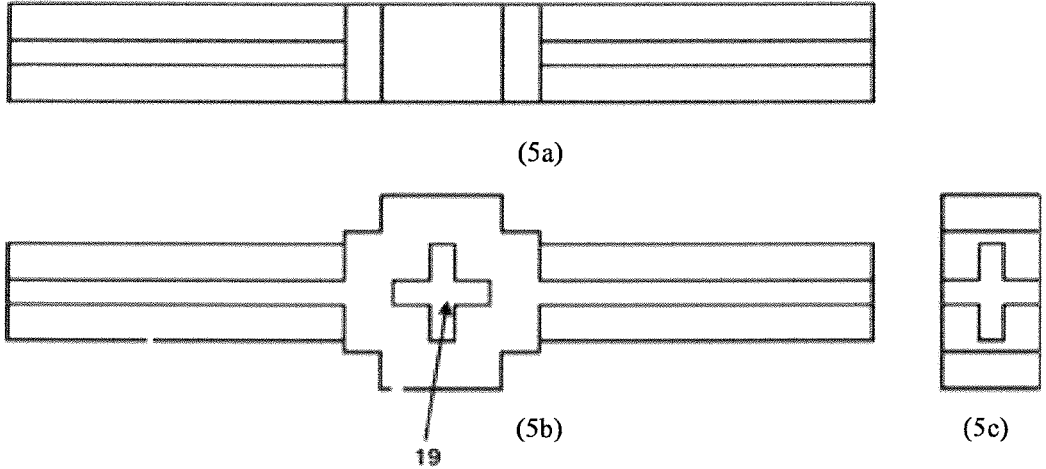
FIG. 5 shows different views 5*a*, 5*b* and 5*c* of the vertical axis including a top, resp. side views of the device according to the invention.
Figure 6:
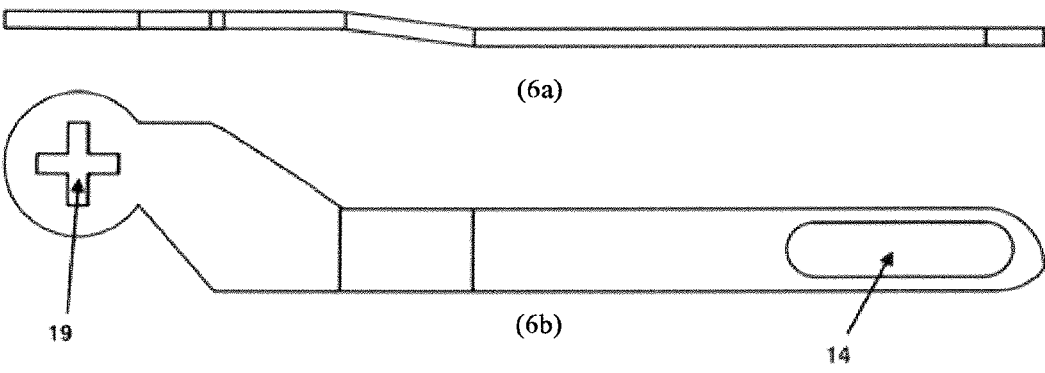
FIGS. 6*a* to 6*c* represent a top view and a side view of an internal arm of the wire placing device used with an elongated aperture in detail of the device according to the invention for tension band wiring fixation.

The main member 1 of the device is associated with a fastening element 3 which is referred to herein as the vertical axis element. This part is connected to the central part of the device 1 by means of a cross shaped connection 19 in its center as shown in FIG. 5. On either side, there are extensions that serve to connect the internal and external arms 4, 5, 4' respectively. The internal arm of the wire placing device used with an elongated aperture in detail of the device for tension band wiring fixation is shown in FIGS. 6*a* to 6*c*.

The device 1 further comprises at least three arms in the wire placing device consisting of a first external arm 5 which is fixed to the vertical axis 3 through said cross shaped connection 19 and has e.g. three holes 7, 7', 7" for a selective optional use. Through these holes, one sleeve is placed for drilling the ulnar shaft and for inserting the wire. Said holes provide the surgeon the opportunity to place two K-Wires with a better biomechanical function.

A second intermediary internal arm 4 having an elongated oval like aperture 14 is also fixed to said vertical axis 3, wherein the elongated aperture allows for drawing the wire distally under the skin of the patient. A third arm 4' which is similar to said second arm 4 is fixed to said vertical axis 3 as well with the same function. These three arms 5, 4, 4' are used for the olecranon fractures osteosynthesis as further set out below.

FIG. 7 represents a top view and a side view of an external arm of the said wire placing device 5 with a series of longitudinally arranged holes in detail of the device according to the invention.

FIG. 8 shows the sleeves-external guides 18 for K-Wires 2 that are cannulated and threated and are fixed to the last part of the main member 1 of the device, with eleven possible positions A, B, . . . K. These are placed parallel to each other and perpendicular to the ulnar bone.

The latter member is associated with a sleeve which serves as a cutting guide 6, represented accordingly in FIG. 9. This element has three holes, one for sleeve position and two K-Wires sockets for its stabilization and two guides for carrying out the V-shaped olecranon osteotomy. This is used for achieving the correct olecranon osteotomy.

7
8

Figure 10:
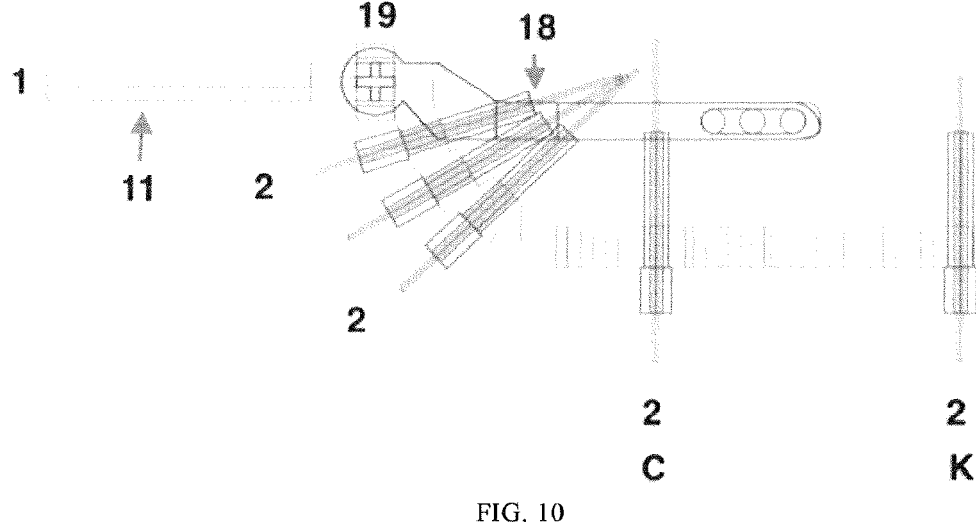
FIG. 10 is a view in a horizontal plane of the device according to the invention showing the said main member with the three optional cannulated sleeves-external guides placed in a different angle with the two K-wires placed in parallel.

The said main member with the three optional cannulated sleeves-external guides placed in a different angle with the two K-wires placed in parallel is shown in FIG. 10.

Figure 11:
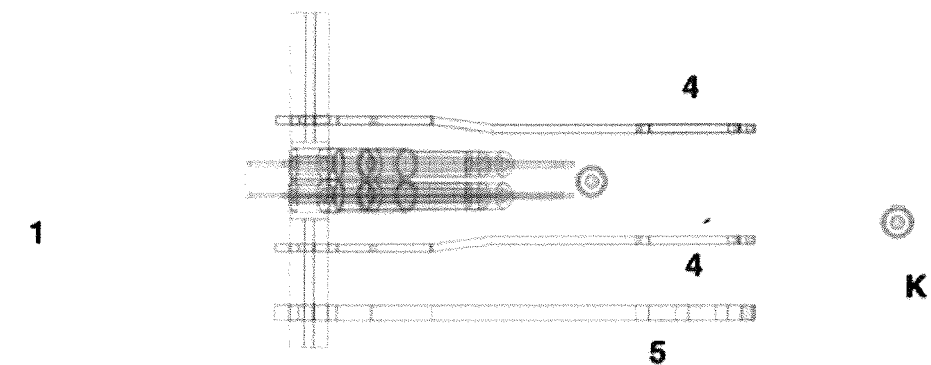
FIG. 11 is a top view of the device according to the invention when assisting in the placement of the wire and the other parts 1, 4 and 5.

The device shown in FIG. 11 is when assisting in the placement of the wire and the other parts 1, 4 and 5.

Figure 12:
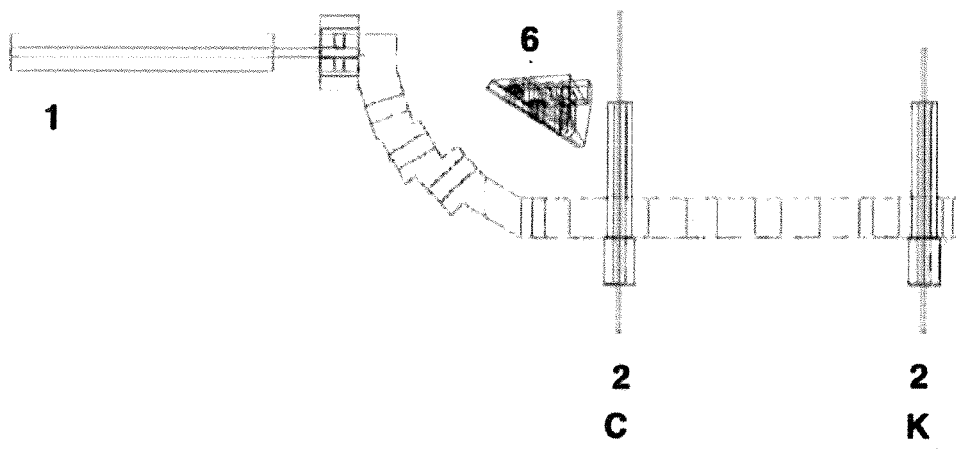
FIG. 12 is a perspective view showing the cannulated sleeve-external guide and the cooperating cutting guide when integrating in the main member of the device, through which the osteotomy of the olecranon is performed.

The cannulated sleeve-external guide and the cooperating cutting guide when integrating in the main member of the device, through which the osteotomy of the olecranon is performed is represented in FIG. 12.

A method of use of a tension band aiming device as defined above for treating an olecranon fracture, is set out hereafter.

First the surgical technique for the olecranon fractures is set out, which is followed by the technique for the olecranon osteotomy without many modifications.

Accordingly, a tension band aiming device is used for treating an olecranon fracture, as schematically set out with the following process steps, successively:

Depending on whether it is the right or left upper extremity, the corresponding anatomical tension band aiming device represented by element 1 is used.

Using sleeves-external guides 2 adjust into the device, two K-Ws with a size of 1.6 mm are placed to the ulnar shaft distally to the fracture keeping a distance of 5 cm between them, to stabilize the device.

Two sleeves are placed at the intermediary part of main member of the device 1 in a specific position and at a suitable angle depending on the morphology of the fracture.

Two K-Ws of said size 1.6 mm are inserted through each sleeve, parallel to each other and at the appropriate angle. The device offers the possibility of placing K-Ws in three different positions—angles always with a distance of 1 cm between them.

The wire placing device 4 is adjusted, which is further entered under the skin of the patient and on either side of the olecranon, embracing it.

An arm over the skin 5 is placed and an additional sleeve creating a hole for the wire to pass through. The device offers the opportunity to make the hole at a different place depending on the morphology of the fracture.

A hole is drilled through the ulna with a 1.6 mm K-wire through the sleeve of approximately 40 mm distal to the fracture line and 5 mm from the posterior cortex.

A 1.2 mm wire, e.g. multi-stranded wire, is passed through the sleeve and the hole.

Assuming the wire has come out on the other side, the sleeve and the arm 5 is removed.

The wire placing device 4 is carefully removed, which draws the wire distally under the skin as it is removed.

Gradually all parts of the device and the initial K-Ws that were placed distally to the fracture for device stabilization are removed.

Finally, after the K-Ws and the wire are placed in the appropriate position with the help of the device, the completion of the internal osteosynthesis i.e. the tension band is proceeded up.

The surgical technique for the olecranon osteotomy with tension band aiming device is described more in detail hereafter.

Depending on whether it is right or left upper extremity, the corresponding anatomical tension band aiming device 1 is used.

Using sleeves-external guides 2 which adjust into the device, two K-Ws with size 1.6 mm are placed in the ulnar shaft with a distance of 5 cm between them, to stabilize the device.

Two proximal sleeves are placed at the intermediary part of main member of the device 1 in a specific position and at a suitable angle.

Two K-Ws with a size of 1.6 mm are inserted from each sleeve which are parallel to each other and at the appropriate angle. The device offers the possibility of placing K-Ws in two different positions—angles always with a distance between them of about 1 cm.

The olecranon two K-Ws and sleeves are removed.

The cutting guide 6 for the chevron osteotomy is adjusted to the aiming device. We stabilize it into the ulna using one K-Wire through the sleeve and two K-Wires through K-Wire socket (size 1.6 mm).

The sleeves and the aiming device are removed. Then the chevron osteotomy is performed with an oscillating saw. The cutting guide offers two possible options for this kind of osteotomy.

At last about Osteotomy osteosynthesis, the aiming device is firstly placed again. This is easy enough because the two K-Ws which stabilize the device into the ulnar shaft were not previously removed.

The two K-Ws with said size of about 1.6 mm are inserted again from each sleeve-external guide 2 to the olecranon.

The section for placing the wire on the device 4 is adjusted, which enters under the skin and on either side of the olecranon, embracing it.

An arm 5 is placed over the skin and an additional sleeve, creating a hole for the wire to pass through.

A hole is drilled through the ulna with a 1.6 mm K-Wire through the sleeve of approximately 40 mm distal to the fracture line and 5 mm from the posterior cortex.

A 1.2 mm wire is passed through the sleeve.

Assuming the wire has come out on the other side, the sleeve and the arm 5 are removed.

The wire placing device 4 is carefully removed, which draws the wire distally under the skin as it is removed.

All parts of the device and the initial K-Ws that were placed distally for the device stabilization are removed gradually.

Finally, after the K-Ws and the wire are placed in the appropriate position with the help of the device, the completion of the internal osteosynthesis, i.e. the tension band, is proceeded.

REFERENCES

1. Schneider M M, Nowak T E, Bastian L, et al. *Tension band wiring in olecranon fractures: The myth of technical simplicity and osteosynthetical perfection. Int Orthop.* 2014; 38(4):847-855. doi:10.1007/s00264-013-2208-7
2. Amir S, Jannis S, Daniel R. *Distal humerus fractures: a review of current therapy concepts. Curr Rev Musculoskelet Med.* 2016; 9(2):199-206. doi:10.1007/s12178-016-9341-z
3. Müller C A. *Tension Band Fixation. AO Trauma ORP.* 2011:1-10.

The invention claimed is:

1. Device for the fixation of fractures with a tension band wiring fixation, characterized in that it comprises a main member (1) and a plurality of adjuvant elements (2, . . . 6) one of which (2) consists of an assisting means for an osteotomy, wherein said main member (1) is composed of a first part (11) as a handling means for handling the device and for connecting a fastening element (3) as a vertical axis element;

an intermediary part (12) wherein a plurality of pairs of holes (7, 7', 7") are formed arranged mutually in line at the same distance of each other at a free end thereof (12) for external guides-sleeves (18) to place K-Wires (2) at a suitable angle (a) depending on the morphology of the fracture, and a further part (13) that is elongated and contains a plurality of linearly arranged apertures (8, 8', . . .) for stabilizing said main member (1) of the device and a cutting guide (6);

the further part (13) additionally comprising a wire placing device that is composed of at least three arms (4, 4', 5), respectively consisting of a first external arm (5) which is fixed to said vertical axis element (3) and has said holes (7, 7', 7") for a selective optional use, through which one sleeve (18) is placed for drilling an ulnar shaft and for inserting a wire (2);

a second intermediary internal arm (4) which has an elongated aperture (14), and is fixed to the said vertical axis element (3) with an elongated aperture for drawing the wire distally under the skin of the patient to be treated;

a third arm (4'), which is fixed likewise to the vertical axis element (3), wherein said three arms (5, 4, 4') are in a mutually cooperating arrangement for osteo-synthesis.

2. Device according to claim 1, wherein said main member (1) of the device is fastened to said vertical axis element (3) at right angles to said vertical axis element.

3. Device according to claim 2, wherein said fastening element (3) is connected to the central part of the main member (1), wherein on either side thereof of the main member extensions are provided for connecting the internal and external arms (4, 5, 4').

4. Device according to claim 1, wherein said wire placing device (4, 4', 5) having its three arms respectively wherein said first external arm (5) has three holes (7, 7', 7") for the selective use, through which said sleeve (18) is placed allowing the insert of a wire (2).

5. Device according to claim 1, wherein said second intermediary internal arm (4) has an elongated oval like hole (14).

6. Device according to claim 1, wherein said third arm (4') is similar to the second arm (4) which is fixed likewise to the vertical axis element (3) with the same function for the olecranon fractures osteosynthesis.

7. Device according to claim 1, wherein said external guides-sleeves (18) for K-Wires (2) that are cannulated and threaded, and that are fixed to said last part of said main member (1) of the device, having said plurality of selectable positions (A, B, . . . K) with said apertures amounting to about eleven (8, 8', . . .) thereof, wherein these guides (18) are placed parallel to each other and perpendicular to said ulnar bone.

8. Device according to claim 1, wherein further comprising a cutting guide (6) associated with said external guide-sleeve (18), the cutting guide (6) comprising three holes (7, 7', 7"), one (7) for sleeve position and two K-Wires sockets, for its stabilization and two guides for carrying out a V-shaped olecranon osteotomy for a correct olecranon osteotomy.

9. Device according to claim 1, wherein two anatomical tension band aiming devices are provided, each one intended for the right or left upper extremity respectively.

10. Method of treating an olecranon fracture, comprising providing a device according to claim 1;

placing two K-Wires to the ulnar shaft distally to the fracture keeping a distance between them, to stabilize the device using sleeves-external guides (2) which adjust into the device, particularly having a size of about 1.6 mm when the distance between said K-wires is less than about 5 cm, placing two sleeves (18, 2) at the intermediary part (12) of said main member (1) of the device in a selected specific position and at a suitable angle (a) depending on the morphology of the fracture, inserting two additional K-Wires, particularly with a size of about 1.6 mm, through each sleeve (18) parallel to each other and at the appropriate angle, adjusting the wire placing device (4), which is entered under the skin of the patient and on either side of the olecranon, embracing it, placing an arm (5) over the skin and an additional sleeve (18) providing a passage for the wire (2) to pass through it, wherein the device allows to provide the said passage at a different place depending on the morphology of the fracture, drilling a hole through the ulna with said K-wire (2) through the sleeve (18), passing a wire-particularly a 1.2 mm multi-stranded wire-through the sleeve (18) and said hole or passage, removing the additional sleeve (18) and the arm (5), removing the wire placing device (4), which draws the wire distally under the skin as it is removed, removing all parts of the device and K-wires that were placed distally to the fracture for device stabilization, completing internal osteosynthesis.

11. Method according to claim 10 comprising providing a device (1) which corresponds to a right or left upper extremity, placing two said K-wires in the ulnar shaft with a distance between them, to stabilize the device, using sleeves-external guides which adjust into the device, placing two proximal sleeves at the intermediary part of said main member (1) of the device in a specific position and at a suitable angle, inserting two said K-wires from each sleeve which are parallel to each other and at the appropriate angle, wherein the device allows placing said K-wires in two different positions-angles, generally with a distance between them of about 1 cm, removing of two said K-wires and sleeves from the olecranon, adjusting the cutting guide (6) for the chevron osteotomy to the aiming device, which is stabilized into the ulna using one K-Wire through the sleeve and two K-Wires through K-Wire socket, particularly of size of about 1.6 mm, and removing the sleeves and the aiming device, after which the chevron osteotomy is performed with an oscillating saw, wherein the said cutting guide (6) allows two possible options for this kind of osteotomy.

12. Method for performing b-Osteotomy osteosynthesis according to claim 10, further comprising replacing the aiming device (1), re-inserting two K-Wires from each sleeve-external guide to the olecranon, adjusting the section for placing the wire on the device (4), which enters under the skin and on either side of the olecranon, embracing it, placing an arm (5) over the skin and an additional sleeve, creating a hole or passage for the wire to pass through, drilling a hole through the ulna with a said K-wire through the sleeve, approximately 40 mm distal to the fracture line and 5 mm from the posterior cortex, passing a wire of approximately 1.2 mm through the sleeve, removing the sleeve and the arm (5), removing the wire placing device (4), thereby drawing the wire distally under the skin as it is removed, removing all parts of the device (1) and the initial said K-wires that were placed distally for the device stabilization, and completing the internal osteosynthesis.

13. A method for performing an osteotomy of the olecranon in a patient in need of such treatment, the method comprising the step of providing a device according to claim 1.

14. The device of claim 1, wherein the plurality of adjuvant elements comprises five adjuvant elements.

15. The device of claim 1, wherein the plurality of pairs of holes comprises three pairs of holes.

16. The device of claim 1, wherein the plurality of linearly arranged apertures (8, 8', . . . ) comprises eleven apertures.

17. The method of claim 10, wherein the device is configured to permit placing said K-Wires in three different positions-angles generally with a distance of about 1 cm between the K-wires.

18. The method of claim 10, wherein the hole is drilled in an ulna approximately 40 mm distal to the fracture line and 5 mm from the posterior cortex.

19. The method of claim 11, wherein the distance between the two said K-wires in the ulnar shaft is about 5 cm.

\* \* \* \* \*